United States Patent [19]

Smith et al.

[11] Patent Number: 4,960,934

[45] Date of Patent: Oct. 2, 1990

[54] AMINE OXIDE PROCESS

[75] Inventors: Kim R. Smith; Joe D. Sauer, Baton Rouge, La.

[73] Assignee: Ethyl Corporation, Richmond, Va.

[21] Appl. No.: 427,780

[22] Filed: Oct. 27, 1989

[51] Int. Cl.$^5$ ............................................ C07C 135/02
[52] U.S. Cl. .................................... 564/298; 544/173; 544/383; 546/192; 546/348; 564/299
[58] Field of Search ................ 564/298, 299; 544/173, 544/383; 546/192, 348

[56] References Cited

FOREIGN PATENT DOCUMENTS 0307184 3/1989 European Pat. Off. ............ 564/298

*Primary Examiner*—Robert V. Hines
*Attorney, Agent, or Firm*—Joseph D. Odenweller

[57] ABSTRACT

The reaction of aqueous hydrogen peroxide with tert-amines to yield tert-amine oxides is catalyzed by the addition of a promoter amount of ammonium carbonate, ammonium bicarbonate or ammonium carbamate or mixtures thereof.

22 Claims, No Drawings

AMINE OXIDE PROCESS

BACKGROUND

It is known to make tert-amine oxides by reacting tert-amines with aqueous hydrogen peroxide Murata et al. U.S. Pat. No. 4,247,480 teach that the reaction rate can be increased by adding carbon dioxide to the reaction mixture. This necessitates injecting a gas which requires gas handling facilities. It would be desirable to be able to promote the reaction rate without the necessity of using additional equipment.

SUMMARY

It has now been discovered that the reaction rate of tert-amines with aqueous hydrogen peroxide can be sharply increased by adding ammonium carbonate, ammonium bicarbonate or ammonium carbamate or mixtures thereof to the reaction mixture.

DESCRIPTION OF THE PREFERRED EMBODIMENTS

A preferred embodiment of the invention is an improvement in the process for making tert-amine oxides by the reaction of a tert-amine capable of forming an amine oxide with aqueous hydrogen peroxide. According to the improvement the reaction rate is increased by conducting the process in the presence of a promoter amount of ammonium carbonate, ammonium bicarbonate or ammonium carbamate or mixtures thereof catalyst.

Any amine can be used in the process that is capable of forming an amine oxide. Examples of these are the tert-amines having the formula $R^1R^2R^3N$ wherein wherein $R^1$, $R^2$ and $R^3$ are independently selected from alkyl groups having 1-30 carbon atoms, cycloalkyl groups containing 5-12 carbon atoms, aryl groups containing 6-12 carbon atoms, aralkyl groups containing 7-12 carbon atoms or any two of $R^1$, $R^2$ and $R^3$ can be joined to form a heterocylic ring or $R^1$, $R^2$ and $R^3$ can be joined to form a pyridine ring. Examples of these are butyldimethylamine, hexyldimethylamine, isobutyldimethylamine, 2-ethylhexyldimethylamine, octyldimethylamine, decyldimethylamine, dodecyldimethylamine, tetradecyldimethylamine, hexadecyldimethylamine, eicosyldimethylamine, docosyldimethylamine, triacontyldimethylamine, tributylamine, butyldiethylamine, isobutyldiethylamine, decylbutylethylamine, hexadecylhexylmethylamine, eicosyldibutylamine, trioctylamine, tridodecylamine, dieicosylethylamine, di-triacontylmethylamine, N,N,-dimethyl-aniline, N-methyl-N-dodecylaniline, cyclopentyldimethylamine, cyclohexyldimethylamine, dicyclohexylmethylamine, cyclododecyldimethylamine, diphenylbutylamine, para-tolyldiethylamine, α-naphtylbutylmethylamine, benzylbutylmethylamine, α-methylbenzylbutylmethylamine, (4-butylbenzyl)octylmethylamine, dibenzylbutylamine, (4-pentyl)benzyldibutylamine, N-butylmorpholine, N-methylmorpholine, N-methylpiperidine, N-dodecylpiperidine, N-octadecylpiperidine, N-triacontylpiperidine, N-methylpiperazine, N-butylpiperazine, N-octylpiperazine, N-phenylpiperidine, N-benzylpiperidine, N-cyclohexylpiperidine, pyridine and the like.

In a more preferred embodiment $R^1$ is a primary alkyl group containing 6-20 carbon atoms and $R^2$ and $R^3$ are methyl or ethyl. Examples of these are hexyl diethylamine, octyl methyl ethylamine, decyl dimethylamine, decyl diethylamine, dodecyl dimethylamine, tetradecyl dimethylamine, hexadecyl dimethylamine, octadecyl dimethylamine, eicosyl dimethylamine and the like.

Another highly preferred class of tert-amines are those in which both $R^1$ and $R^2$ are primary alkyl groups containing 6-20 carbon atoms and $R^3$ is methyl or ethyl. Examples of these are dihexyl ethylamine, dioctyl methylamine, didecyl methylamine, octyl decyl methylamine, decyl dodecyl methylamine, didodecyl methylamine, dieicosyl methylamine and the like.

Any aqueous hydrogen peroxide can be used including those containing 3-100 percent $H_2O_2$. Preferably the hydrogen peroxide is 20-70 weight percent active $H_2O_2$. When the tertamine is linear $C_{8-20}$ alkyl dimethylamine, it is preferred that the aqueous hydrogen peroxide be about 20-40 weight percent $H_2O_2$ to avoid gel formation. Alternatively, more concentrated hydrogen peroxide can be used and additional water either added initially or co-fed to maintain a stirrable reaction mixture. In this mode of operation it is the "net" $H_2O_2$ concentration, taking into account the additional water, that controls gel and should be kept in a gel-free range. For example, co-feeding 100 g of 50 percent aqueous hydrogen peroxide and 100 g of water gives a "net" 25 percent aqueous hydrogen peroxide. Likewise prior addition of 100 g of water to the tert-amine followed by feeding 100 grams of 50 percent aqueous hydrogen peroxide gives a "net" 25 percent aqueous hydrogen peroxide. Likewise, co-solvents such as lower alcohol, e.g., isopropanol, isobutanol and the like, can be used to avoid gelation.

The amount of hydrogen peroxide should be at least a stoichiometric amount. A useful range is about 1-5 moles of $H_2O_2$ and more preferably 1-1.5 mole of $H_2O_2$ per mole of tert-amine. A highly preferred amount is about 1.0-1.3 moles of $H_2O_2$ and especially about 1.05-1.2 moles of $H_2O_2$ per mole of tert-amine. Any substantial amount of unreacted $H_2O_2$ remaining after the reaction can be destroyed by the addition of a reducing agent or a peroxide decomposition catalyst.

When the process is conducted using a di-linear alkyl methylamine, the process can be carried out using more concentrated aqueous hydrogen peroxide such as about 45-70 weight percent hydrogen peroxide. When the di-linear alkyls contain about 6-12 carbon atoms each, the reaction mixture will remain substantially gel free. When the di-linear alkyls contain 14 or more carbon atoms the reaction mixture will set up to a dry flakeable solid on cooling.

The catalyst can be ammonium carbonate, ammonium bicarbonate or ammonium carbamate. Ammonium carbonate exists as an equilibrium mixture of ammonium bicarbonate and ammonium carbamate formed when $NH_3$ and $CO_2$ are reacted or by subliming a mixture of calcium carbonate and ammonium sulfate. Reference to "ammonium carbonate" catalyst in the present invention includes all forms in which it might exist such as mixtures of ammonium bicarbonate and ammonium carbamate.

The reaction is conducted by adding the aqueous hydrogen peroxide to the tert-amine. The addition rate should be adjusted to prevent a build-up of unreacted hydrogen peroxide in the reaction vessel. The catalyst is preferably added to the tert-amine in the reaction vessel at the start of the hydrogen peroxide addition. Alternatively the catalyst can be dissolved in the aqueous hydrogen peroxide, although this is not the preferred mode of operation, especially when highly concentrated hydrogen peroxides are used.

The amount of catalyst should be a promoter amount. A useful range in which to operate is about 0.05-5 weight percent catalyst based on the initial tert-amine charge. A preferred range is about 0.1-1 weight percent catalyst.

The reaction temperature can range from about 20° C. or lower up to about 120°. Above 120° C., amine oxides have been reported to decompose. A preferred temperature range is about 20°-80° C. It has been found that nitrosamine formation which usually occurs in the synthesis of amine oxides, can be greatly decreased by conducting the reaction at about 20°-40° C. or at least starting the reaction at 20°-40° C. until up to one-half of the aqueous hydrogen peroxide has been added and then allowing the temperature to rise to 60°-80° C. to complete the reaction.

Another embodiment of the invention is a process for making a trialkylamine oxide dihydrate, said process comprising reacting a tert-amine having the formula $R^4R^5R^6N$ wherein $R^4$, $R^5$ and $R^6$ are independently selected from primary alkyls containing 1-30 carbon atoms, primary aralkyls containing 7-12 carbon atoms, hydroxyalkyls containing 2-4 carbon atoms and tert-amines wherein any two of $R^4$, $R^5$ or $R^6$ taken together form a morpholine or piperidine ring with an aqueous hydrogen peroxide containing 50-90 weight percent active $H_2O_2$ at a temperature of about 20° C. up to about 100° C., in the presence of a promoter amount of ammonium carbonate, ammonium bicarbonate or ammonium carbamate, at least part of said reaction being conducted in an organic solvent selected from organic esters, liquid aliphatic hydrocarbons containing 6-20 carbon atoms, aromatic hydrocarbons containing 6-8 carbon atoms, cycloaliphatic hydrocarbons containing 6-8 carbon atoms, aromatic halohydrocarbons containing 6-8 carbon atoms, dimethylformamide, diethylformamide, dimethylacetamide, diethyl acetamide and mixtures thereof, said solvent being present in an amount that maintains a fluid stirrable reaction mixture and, if necessary, distilling water from or adding water to said reaction mixture to achieve a water/tert-amine oxide ratio of about 1.9-2.1/1.0 and recovering said tert-amine oxide dihydrate from said reaction mixture.

The phrase "at least part of said reaction" means that all of the desired amount of the organic solvent can be added at the start of the reaction or it can be added incrementally during the course of the reaction or it can be added at the end of the reaction. In practice, it is preferred to add the solvent as needed during the course of the reaction to prevent gelling of the reaction mixture. This is usually not encountered until amine conversion is in excess of 50 percent complete and more often in excess of 75 percent complete.

Any of a broad range of tert-amines can be used in this embodiment. The preferred tert-amines include trialkylamines in which $R^4$, $R^5$ and $R^6$ are alkyl containing 1-30 carbon atoms. Examples of these are trimethylamine, triethylamine, tri-n-butylamine, isobutyl dimethylamine, trihexyl amine, di-n-dodecyl isobutylamine, tri-n-dodecylamine, 2-ethylhexyl dimethylamine, n-octadecyl di-n-propylamine, n-eicosyl diisobutylamine, n-triacontyl isobutyl methylamine and the like.

Other suitable tert-amines include those in which one or more of the R groups are aralkyl containing 7-12 carbon atoms. Examples of these are benzyl dimethylamine, dibenzyl ethylamine, 4-tert-butyl benzyl diisobutylamine.

Likewise hydroxyalkyl substituted tert-amines can be used in the process to prepare the corresponding tert-amine oxide dihydrates. Such tert-amines include triethanolamine, dodecyl diethanolamine, didecyl ethanolamine, tetradecyl di-(2-ethyl ethanol) amine and the like.

Other tert-amines suitable for use in the process are those in which any two of $R^4$, $R^5$ and $R^6$ taken together form a morpholine or piperidine ring. These include N-methyl morpholine, N-ethyl morpholine, N-decyl morpholine, N-dodecyl morpholine, N-tetradecyl morpholine, N-hexadecyl morpholine, N-ethanol morpholine, N-methyl piperidine, N-ethyl piperidine, N-octyl piperidine, N-decyl piperidine, N-dodecyl piperidine, N-tetradecyl piperidine and the like.

A preferred class of tert-amines are those having the formula $R^4R^5R^6N$ wherein $R^4$ is a primary alkyl having about 8-24 carbon atoms, $R^5$ is a primary alkyl having either 1-2 carbon atoms or having 8-24 carbon atoms and $R^6$ is methyl or ethyl. Representative examples of these are:
n-octyl diethylamine
n-decyl dimethylamine
n-decyl diethylamine
n-dodecyl dimethylamine
n-dodecyl diethylamine
n-tetradecyl dimethylamine
n-hexadecyl diethylamine
n-octyldecyl dimethylamine
n-eicosyl dimethylamine
di-(n-octyl)methylamine
di-(n-decyl)methylamine
di-(n-dodecyl)ethylamine
di-(n-tetradecyl)methylamine
di-(n-hexadecyl)ethylamine
di-(n-octadecyl)methylamine
di-(n-eicosyl)methylamine
n-octyl n-dodecyl methylamine
n-decyl n-octadecyl ethylamine
n-decyl n-eicosyl ethylamine
and the like including mixtures thereof.

Of the above a still more preferred class of tert-amines consists of those in which $R^4$ is a $C_{8-24}$ primary alkyl, $R^5$ is methyl or a $C_{8-24}$ primary alkyl and $R^6$ is methyl. Examples of these are:
octyl dimethylamine
decyl dimethylamine
dodecyl dimethylamine
tetradecyl dimethylamine
hexadecyl dimethylamine
eicosyl dimethylamine
docosyl dimethylamine
tetracosyl dimethylamine
dioctyl methylamine
didecyl methylamine
didodecyl methylamine
decyl dodecyl methylamine
ditetradecyl methylamine
tetradecyl octyl methylamine
and the like including mixtures thereof.

In this embodiment the preferred aqueous hydrogen peroxide is about 50-90 weight percent $H_2O_2$. A more preferred concentration is about 50-75 weight percent and most preferably about 70 weight percent.

The amount of aqueous hydrogen peroxide should be at least about a stoichiometric amount. For example, at least about 0.9 moles and preferably 1.0 mole up to 5 moles of hydrogen peroxide per mole of tert-amine. Good results can be achieved using about 1.1–1.5 mole parts and especially 1.0–1.3 moles of aqueous hydrogen peroxide per mole of tert-amine and more preferably about 1.05–1.2 mole parts of hydrogen peroxide per mole of tert-amine.

The reaction is conducted by adding the aqueous hydrogen peroxide to the stirred tert-amine. Inclusion of a small amount of a chelating agent such as diethylene triaminepentaacetic acid improves the reaction rate. The reaction temperature can vary from ambient up to 100° C. or higher. The reaction can be started at a moderate temperature, e.g., 25–50° C. and the temperature slowly increased to about 60°–75° C. as the reaction proceeds. In most cases, little advantage will be obtained through the use of temperatures in excess of about 100° C. In fact, temperatures over 100° C. may be detrimental as the amine oxide formed will decompose.

The preferred embodiment would be to add the hydrogen peroxide at a controlled rate to the amine containing the catalyst. By "controlled rate" it is meant to add the hydrogen peroxide as it reacts rather than all at once so that the amount of hydrogen peroxide in the reaction mixture does not reach a hazardous level. The oxidation of the amine can be carried out at atmospheric, superatmospheric or subatmospheric pressure as may be desirable. In most cases, operation at substantially atmospheric pressure will be found to be most convenient.

As in the previous embodiment, the catalyst is preferably added to the tert-amine prior to starting the hydrogen peroxide feed.

Addition time will depend on temperature and scale. Preferably, the hydrogen peroxide addition is not so rapid that a large accumulation of unreacted hydrogen peroxide occurs. Addition times in the range of 0.1–8 hours for small scale runs (on the order of 1 liter) up to 1–24 hours for large scale commercial operations are generally satisfactory. If thickening occurs during the reaction, organic solvent can be added as needed to maintain a stirrable reaction mixture.

Following the hydrogen peroxide addition, the reaction mixture can be stirred at 60° C. or higher for a period to be certain that the reaction has gone to completion. A ride time of about 1–24 hours is usually adequate. During this time, following hydrogen peroxide addition, organic solvent can be added to the reaction as needed in order to maintain a fluid stirrable reaction mixture.

The reaction mixture at completion will contain an amount of water that will vary with the amount and concentration of the hydrogen peroxide used in the process. For example, if 1.1 moles of 50 weight percent aqueous hydrogen peroxide is reacted with 1.0 mole of tert-amine, the reaction product will contain about 52 g (2.89 moles) of water. This exceeds the amount needed to form the dihydrate so part of this must be co-distilled out with some of the organic solvent such that the final water/amine oxide mole ratio is close to 2/1, e.g. 1.9–2.1/1.0. With a water-immiscible solvent, this can be done using a Dean-Stark water trap which returns the organic solvent. Alternatively additional organic solvent can be merely added during the distillation to prevent any gel formation and to maintain a stirrable reaction mixture.

In a more preferred embodiment the concentration of the aqueous hydrogen peroxide is about 70 weight percent. In this mode of operation, reaction of 1.1 moles of hydrogen peroxide with 1.0 moles of tert-amine will result in a reaction mixture containing 34 g (1.9 moles) of water which is very close to the desired 2/1 water/amine oxide mole ratio. In this most preferred embodiment, it is not necessary to distill out any of the water. The tert-amine oxide dihydrate can be merely precipitated by cooling the solution. Alternatively, the organic solvent can be distilled out leaving the tert-amine oxide dihydrate as a residual product.

Good results have been achieved by conducting the process at least at the end in an organic ester. This is an ester formed from an organic acid and an alcohol, aliphatic polyol or arylhydroxy compound.

The organic ester functions both as a polar, organic solvent for the preparation of the tert-amine oxide dihydrate and as a crystallization medium following completion of the reaction. The characteristics of the solvent are preferably such that the amine oxide dihydrate and its parent amine are both soluble at the reaction temperatures but the amine oxide dihydrate is not completely soluble at ambient temperature or lower. Thus, any organic ester which meets these criteria can be used in the practice of the present invention.

Preferred organic esters suitable for use in the invention are those having the formula:

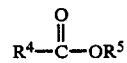

wherein $R^4$ is hydrogen, $(C_{1-12})$ alkyl, $(C_{5-8})$ cycloalkyl, $(C_{3-24})$ alkenyl in which there is no unsaturation in the alkenyl group in conjugation with the carbonyl atom contained in the ester, phenyl, phenyl substituted with one or more $(C_{1-12})$ alkyl or $(C_{1-4})$ lower alkoxy, $(C_{7-12})$ aralkyl, benzyl substituted with one or more $(C_{1-12})$ alkyl or $(C_{1-4})$ lower alkoxy, $(C_{7-12})$ alkaryl and $R^5$ is $(C_{1-12})$ alkyl, $(C_{5-8})$ cycloalkyl, $(C_{3-24})$ alkenyl, phenyl, phenyl substituted with one or more $(C_{1-12})$ alkyl or $(C_{1-4})$ lower alkoxy, $(C_{7-12})$ aralkyl, benzyl substituted with one or more $(C_{1-12})$ alkyl or $(C_{1-4})$ lower alkoxy, or $(C_{7-12})$ alkaryl.

Examples of suitable alkyl groups are methyl, ethyl, n-propyl, isopropyl, n-butyl, isobutyl, sec-butyl, tert-butyl, n-amyl, and the various positional isomers thereof, and likewise the corresponding straight and branched chain isomers of hexyl, heptyl, octyl, nonyl, decyl, undecyl and dodecyl.

Examples of cycloalkyl groups are cyclopentyl, cyclohexyl and cyclooctyl.

Some examples of alkenyl groups are 1-propenyl, 1butenyl, 2-butenyl, 3-butenyl, and the corresponding branchedchain isomers thereof as, for example, 1-isobutenyl, 2-isobutenyl, 2-sec-butenyl, including 1-methylene-2-propenyl, and the various isomers of pentenyl, hexenyl, heptenyl, octenyl, nonenyl, decenyl, undecenyl, and dodecenyl, including 3,3-dimethyl-1butenyl, 2,3-dimethyl-1-butenyl, 2,3-dimethyl-2-butenyl, 2,3-dimethyl-3-butenyl, 1-methyl-1-ethyl-2-propenyl and the like.

Examples of $(C_{1-4})$ lower alkoxy groups are methoxy, ethoxy, propoxy and butoxy.

Examples of aralkyl groups are benzyl, phenylethyl, 1-phenylpropyl, 2-phenylpropyl, 3-phenylpropyl, 1- and 2-isomers of phenylisopropyl, 1-, 2-, and 3-isomers of phenylbutyl, and the like.

Examples of alkaryl groups are tolyl, 2,3-xylyl, 2,4-xylyl, 2,5-xylyl, 2,6-xylyl, 3,4-xylyl, 3,5-xylyl, o, m, and p-cumenyl, mesityl, o, m, and p-ethylphenyl.

Representative examples of preferred organic esters which can be used in the practice of the present invention include methyl formate, ethyl formate, n-propyl formate, n-butyl formate, methyl acetate, ethyl acetate, n-propyl acetate, isopropyl acetate, n-butyl acetate, sec-butyl acetate, tert-butyl acetate, isobutyl acetate, n-amyl acetate, n-hexyl acetate, n-octyl acetate 2-ethylhexyl acetate, 3-ethyl-pentyl acetate, methyl propanoate, ethyl propanoate, methyl butyrate, ethyl butyrate, ethyl isobutyrate, methyl hexanoate, ethyl hexanoate, propyl hexanoate, amyl hexanoate, hexyl hexanoate, isopropyl caprylate, cyclopentyl acetate, cyclohexyl acetate, cyclopentyl propanoate, cyclohexyl propanoate, cyclopentyl butyrate, cyclohexyl butyrate, cyclopentyl hexanoate and the like.

Liquid aliphatic hydrocarbons containing 6-20 carbon atoms and cycloaliphatic hydrocarbons containing 6-8 carbon atoms can be used as the inert solvent. Of these the preferred contain 6-8 carbon atoms such as hexane, isohexane, 2-ethylhexane, heptane, octane, isooctane, cyclohexane, cyclooctane and the like.

Aromatic halohydrocarbons containing 6-8 carbon atoms and 1-2 halogen atoms can also be used as the solvent. These include chlorobenzene, dichlorobenzene, bromobenzene, chlorotoluene, 2,4-dichlorotoluene and the like.

Other useful solvents include the highly polar solvents dimethyl formamide, dimethyl acetamide, diethyl formamide, diethyl acetamide and mixtures thereof. Dimethyl sulfoxide is another useful highly polar solvent.

Mixtures of solvents can also be used with good results. For example a non-polar solvent such as toluene results in a precipitate of very fine gel-like crystals of trialkylamine oxide dihydrate. By including a small amount (e.g. 2-10 weight percent) of a polar solvent such as an alcohol, e.g. isopropanol the crystal size can be increased making recovery by filtration much faster.

Other possible co-solvents for use with the non-polar aromatic and aliphatic hydrocarbon solvents are methanol, ethanol, isobutanol, dimethylformamide, dimethyl acetamide, dimethyl sulfoxide and the like. Other possible combinations are xylene/dimethyl formamide, benzene/chlorobenzene, heptane/ethyl acetate, cyclohexane/isobutanol, cyclohexane/diethyl acetamide, isooctane/dimethyl sulfoxide and the like.

The amount of organic solvent used should be an amount sufficient to provide a readily fluid reaction mixture to avoid gelling of the reaction mass. Generally, the weight of solvent used is from less than the weight of the amine reactant to several times the weight of the amine. Usually not more than about five to ten times the weight of the amine reactant of solvent need be used. In most cases, a weight of solvent of from about 1 to about 4 times the weight of amine reactant is most convenient.

Amine oxide dihydrates prepared from the parent tert-amine which have been oxidized with 65-70% hydrogen peroxide are usually soluble in the solvent, especially the organic esters, under reaction conditions and crystallize as dihydrates when cooled. Upon completion of the reaction, additional organic solvent can be added and used as a crystallization medium or the solvent may be removed by distillation or evaporation at atmospheric or reduced pressure. The molten form of the product may be readily extruded or flaked. Temperatures should be kept under about 130° C. to avoid decomposition. In either case, the product is the dihydrate of the amine oxide. If a more dilute solution of hydrogen peroxide is used, e.g., 50 weight percent hydrogen peroxide, additional organic solvent can be added to the crude reaction mass which consists mainly of amine oxide, water and organic solvent upon completion of the reaction to permit removal of sufficient water via an azeotrope to obtain the amine oxide dihydrate. If aqueous solutions of hydrogen peroxide are used in which the concentration of hydrogen peroxide is in excess of approximately 70 weight percent, sufficient water must be added to the reaction mass during or after the reaction to bring the final water/tert-amine oxide mole ratio to about 2/1, e.g. 1.9-2.1/1.0. Such amounts are readily ascertainable by one skilled in the art.

The following examples show how the process is conducted.

EXAMPLE 1

In a peroxide passivated glass reaction flask was placed 100 g tetradecyl dimethylamine and 0.5 g ammonium carbonate. The mixture was heated while stirring to 65° C. at which time 23 g of 70 weight percent aqueous hydrogen peroxide was added over a 5-minute period. The reaction mixture was then heated to 75° C. and stirring was continued for two hours while adding ethyl acetate as required (total added 40 mL) to maintain a fluid reaction mixture. Amine conversion to amine oxide was determined by NMR to be 95 percent complete.

EXAMPLE 2

This is a comparative example showing the same reaction as in Example 1 but without the added ammonium carbonate.

In a peroxide passivated glass reaction flask was placed 100 g tetradecyl dimethylamine and 0.5 g of diethylenetriamine pentaacetic acid which is reported to be a promoter for the reaction. The stirred mixture was heated to 65° C. at which time 23 g of 70 weight percent aqueous hydrogen peroxide was added over a five-minute period. The mixture was heated to 75° C. and stirring was continued for two hours while adding ethyl acetate as needed (total 40 mL added) to maintain a fluid mixture. Analysis by NMR showed that only 80 percent of the amine was converted to amine oxide.

The comparative tests establish the catalytic effect of adding ammonium carbonate to the reaction of tert-amine with aqueous hydrogen peroxide to produce tert-amine oxide.

We claim:

1. In a process for making a tert-amine oxide by the reaction of a tert-amine capable of forming an amine oxide with aqueous hydrogen peroxide, the improvement comprising conducting said reaction in the presence of a promoter amount of ammonium carbonate, ammonium bicarbonate or ammonium carbamate or mixtures thereof as a catalyst whereby the reaction rate is increased.

2. A process of claim 1 wherein said tert-amine has the formula $R^1R^2R^3N$ Wherein $R^1$, $R^2$ and $R^3$ are independently selected from alkyl groups having 1-30 carbon atoms, cycloalkyl groups containing 5-12 carbon atoms, aryl groups containing 6-12 carbon atoms, aralkyl groups containing 7-12 carbon atoms or any two of $R^1$, $R^2$ and $R^3$ can be joined to form a heterocylic ring or $R^1$, $R^2$ and $R^3$ can be joined to form a pyridine ring.

3. A process of claim 2 wherein $R^1$ is a primary alkyl group containing 8–24 carbon atoms and $R^2$ and $R^3$ are methyl or ethyl.

4. A process of claim 3 wherein said tert-amine is decyl dimethylamine.

5. A process of claim 3 wherein said tert-amine is dodecyl dimethylamine.

6. A process of claim 3 wherein said tert-amine is tetradecyl dimethylamine.

7. A process of claim 3 wherein said tert-amine is hexadecyl dimethylamine.

8. A process of claim 3 wherein said tert-amine is octadecyl dimethylamine.

9. A process of claim 2 wherein $R^1$ and $R^2$ are primary alkyl groups containing 8–24 carbon atoms and $R^3$ is methyl or ethyl.

10. A process of claim 9 wherein said tert-amine is dioctyl methylamine.

11. A process of claim 9 wherein said tert-amine is didecyl methylamine.

12. A process of claim 9 wherein said tert-amine is didodecyl methylamine.

13. A process for making a trialkylamine oxide dihydrate, said process comprising reacting a tert-amine having the formula $R^4R^5R^6N$ wherein $R^4$, $R^5$ and $R^6$ are independently selected from primary alkyls containing 1–30 carbon atoms, primary aralkyls containing 7–12 carbon atoms, hydroxyalkyls containing 2–4 carbon atoms and tert-amines wherein any two of $R^4$, $R^5$ or $R^6$ taken together form a morpholine or piperidine ring, with an aqueous hydrogen peroxide containing 50–90 weight percent active $H_2O_2$ at a temperature of about 20° C. up to about 100° C., in the presence of a promoter amount of ammonium carbonate, ammonium bicarbonate or ammonium carbamate or mixtures thereof, at least part of said reaction being conducted in an organic solvent selected from organic esters, liquid aliphatic hydrocarbons containing 6–20 carbon atoms, aromatic hydrocarbons containing 6–8 carbon atoms, cycloaliphatic hydrocarbons containing 6–8 carbon atoms, aromatic halohydrocarbons containing 6–8 carbon atoms, dimethylformamide, diethylformamide, dimethylacetamide, diethyl acetamide and mixtures thereof, said solvent being present in an amount that maintains a fluid stirrable reaction mixture and, if necessary, distilling water from or adding water to said reaction mixture to achieve a water/tert-amine oxide ratio of about 1.9–2.1/1.0 and recovering said tert-amine oxide dihydrate from said reaction mixture.

14. A process of claim 13 wherein said solvent is a $C_{1-12}$ alkyl $C_{1-18}$ fatty acid ester.

15. A process of claim 13 wherein $R^4$ and $R^5$ are independently selected from primary alkyl groups containing 8–24 carbon atoms and $R^6$ is a methyl group, or $R^4$ is selected from primary alkyl groups containing 8–24 carbon atoms and $R^5$ and $R^6$ are methyl groups.

16. A process of claim 15 wherein said solvent is a $C_{1-12}$ alkyl $C_{1-18}$ fatty acid ester.

17. A process of claim 16 wherein said solvent is ethyl acetate and said hydrogen peroxide is about 70 weight percent $H_2O_2$.

18. A process of claim 17 wherein said tert-amine is dodecyl dimethylamine.

19. A process of claim 17 wherein said tert-amine is tetradecyl dimethylamine.

20. A process of claim 17 wherein said tert-amine is hexadecyl dimethylamine.

21. A process of claim 1 wherein said catalyst is an equilibrium mixture of ammonium bicarbonate and ammonium carbamate.

22. A process of claim 13 wherein said catalyst is an equilibrium mixture of ammonium bicarbonate and ammonium carbamate.

* * * * *